United States Patent [19]
Benz

[11] Patent Number: 4,796,323
[45] Date of Patent: Jan. 10, 1989

[54] ELECTRIC TOOTHBRUSH

[76] Inventor: Dieter Benz, Hirschstrasse 21, 7900 Ulm, Fed. Rep. of Germany

[21] Appl. No.: 948,051

[22] Filed: Dec. 31, 1986

Related U.S. Application Data

[63] Continuation-in-part of Ser. No. 716,235, Mar. 26, 1985, abandoned, which is a continuation of Ser. No. 379,575, May 17, 1982, abandoned.

[30] Foreign Application Priority Data

May 21, 1981 [DE] Fed. Rep. of Germany ....... 3120300
Mar. 31, 1982 [DE] Fed. Rep. of Germany ....... 3211984

[51] Int. Cl.$^4$ .............................................. A46B 13/02
[52] U.S. Cl. ...................................... 15/23; 200/61.52
[58] Field of Search ...................... 15/23, 24; 200/5 B, 200/61, 45 R, 61.52

[56] References Cited

U.S. PATENT DOCUMENTS

| | | | |
|---|---|---|---|
| 2,310,626 | 2/1943 | Gold | 15/23 |
| 2,618,797 | 11/1952 | Grover | 15/23 |
| 3,451,086 | 6/1969 | Burgett | 15/23 |
| 4,275,749 | 6/1981 | Caroli | 15/23 |

*Primary Examiner*—Edward L. Roberts
*Attorney, Agent, or Firm*—Michael J. Striker

[57] ABSTRACT

Electric toothbrush includes a hollow handle and a rotary brush connected to the handle. A gravity-induced movement responsive switch, such as mercury switch, is located within the handle, and a hand-operated switch is located on the outer surface of the handle. A user by operating a hand-operated switch sets the brush to a lower row of teeth or an upper row of teeth thus switching over an electromotor located within the handle whereas the mercury switch automatically reverses the direction of rotation of the electromotor shaft depending upon respective tilted positions of the handle.

3 Claims, 3 Drawing Sheets

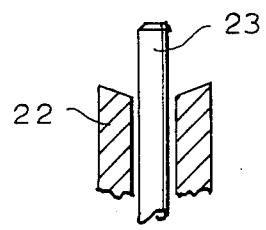
F I G. 7
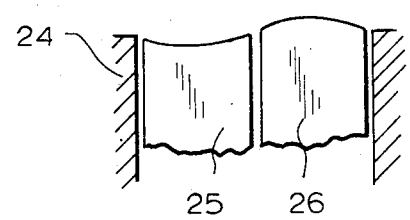
F I G. 8
F I G. 9
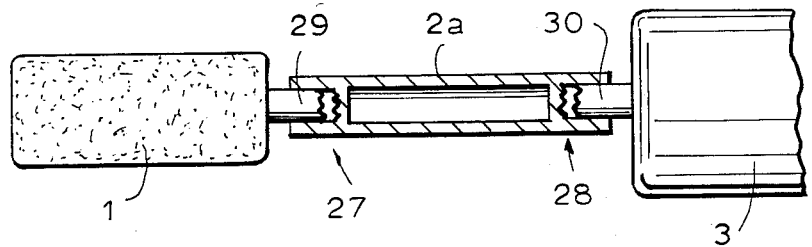

ELECTRIC TOOTHBRUSH

CROSS-REFERENCE TO RELATED APPLICATIONS

This application is continuation-in-part of application Ser. No. 716,235 filed Mar. 26, 1985, now abandoned, which is a continuation of application Ser. No. 379,575 filed May 17, 1982 and now abandoned.

BACKGROUND OF THE INVENTION

The present invention relates to an electric toothbrush.

Electric toothbrushes are, of course, known in the art and used in practice. One of the toothbrushes is disclosed, for example in U.S. Pat. No. 4,163,30.

The toothbrush shown in the above patent includes an elongated body member which serves as a handle when the toothbrush is manually held, and a cylindrical brush connected to an electromotor accommodated in the elongated body and adapted to rotate about the axis of the brush. The toothbrush is provided with a protecting bracket to protect a user's cheek from contacting the toothbrush during its rotation. The toothbrush is provided with a switch which is operated to change the direction of rotation of the brush in response to gravity-induced movement of the handle, depending on the position to which the handle is tilted by a user.

Such known toothbrush, however, has been found rather impractical because a user should always turn or tilt the toothbrush into an exact position in order to ensure a proper direction of rotation of the brush and thus to make it operate properly. (The toothbrush has the following indications: "red" corresponds to a flesh surface and "white" corresponds to a teeth surface). Therefore, it has been found that the toothbrush provided with a reversible switch is not very suitable and has rather complex construction.

Electric toothbrushes disclosed, for example in DO=OS No. 3,011,534; DE-AS No. 1,287,675; DE=GM No. 1,797,828; GB-PS No. 1,406,314; U.S. Pat. No. 3,451,086; DE-OS No. 2,703,401, and U.S. Pat. No. 3,588,936 have been also considered not very practical.

SUMMARY OF THE INVENTION

It is an object of the present invention to provide an improved electric toothbrush.

It is another object of the invention to provide a reliably operating electric toothbrush which is easily operated without requiring many maneuvering actions by a user whereby a user merely switches the toothbrush on for cleaning upper or lower teeth and the toothbrush rotates automatically in a required direction (from "red" to "white").

The objects of the invention are attained by a motor driven electric toothbrush comprising a housing serving as a grip and accommodating an electric motor having a drive shaft; a rotary brush connected to an end of said drive shaft; at least one gravity-induced movement-responsive first switch positioned in said housing and having a switching path formed between two end points serving as contacts of said first switch, and a second switch, each switch switching a direction of rotation of said brush, said second switch being a manually actuated hand switch having an actuating element, said housing having a side wall, said second switch being positioned on said side wall, said switching path being curved, and theoretically having a chord between the ends of the curve, whereby said manually operated switch is arranged in the region of the central transverse axis which is positioned on the longitudinal plane in which said chord lies, and a chord of said switching path forms with an axis of elongation of said housing an angle between 60° and 90° said housing having a guide which forms said switching path and a ball guided in said guide so that said housing may be tilted by an angle between 5° and 15° to change the direction of rotation of said brush.

The operation of the toothbrush of the invention is carried out as follows:

1. Switching on of the manually operated switch on for cleaning upper jaw teeth and automatically switching the toothbrush on by tilting the handle by a user via the gravity-induced movement switch for cleaning an inner side of the teeth and outer side of the teeth, such as (a) right-directed running=the brush rotates to the left outwardly, (b) left-directed running=the brush rotates to the left inwardly, (c) right-directed running=the brush rotates to the right inwardly, (d) left-directed running=the brush rotates to the right outwardly.

2. Switching on of the manually operated switch on for cleaning lower jaw teeth and automatically switching the toothbrush on by tilting the handle via the gravity-induced movement switch for cleaning the inner side of the teeth and outer side of the teeth, such as (a) left-directed running=the brush rotates to the left outwardly, (b) right-directed running=the brush rotates to the left inwardly, (c) left-directed running=the brush rotates to the right inwardly, (d) right-directed running=the brush rotates to the right outwardly.

It is to be noted that the manually operated switch used for reversing the electromotor for cleaning upper jaw teeth or lower jaw teeth may be also utilized for switching the electromotor on and off. It is understood that an additional switch may be also provided for switching the electromotor on and off.

The hollow body may have an outer surface inclined toward the brush, the tumbler being positioned on said inclined surface.

The gravity-induced movement responsive switch may be a mercury switch.

The switching path of the gravity-induced movement responsive switch may be straight or curved.

According to further features of the invention the gravity-induced movement responsive switch means may include a housing positioned in the hollow body or handle of the toothbrush. The aforementioned housing may extend substantially normally to the elongation of the hollow body.

The toothbrush may further include an intermediate member interconnected between the hollow body and the brush. The intermediate member at one end thereof may be disengageably coupled to the end of the rotary brush whereas at another end thereof said member is disengageably coupled with an end of the electromotor shaft.

Another end of the intermediate member may be mounted to the electromotor shaft by a force-locking connection. One end and another end of the intermediate member may be respectively connected to the electromotor shaft and to the brush by a spur-gearing means.

The housing of the gravity-induced movement switch means may include a contact element movable in the housing. The contact element may be made out of ferromagnetic material. The housing of the switch may be provided with oppositely positioned therein contact surfaces connected to the electric circuit of the electromotor, the contact element selectively contacting said oppositely positioned contact surfaces upon the opposite tilted positions of the handle of the electric toothbrush. The contact element may be formed as a ball.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 7 is a partial schematic view of a hand-operated switch for right or left-directed running of the toothbrush;

FIG. 8 is a partial schematic view of the hand-operated switch according to another embodiment; and FIG. 9 is a partial side view similar to FIG. 1 of the electric toothbrush, in which an intermediate element coupling the toothbrush with the handle is provided with coupling gearings.

DETAILED DESCRIPTION OF THE PREFERRED EMBODIMENTS

Figure 1:
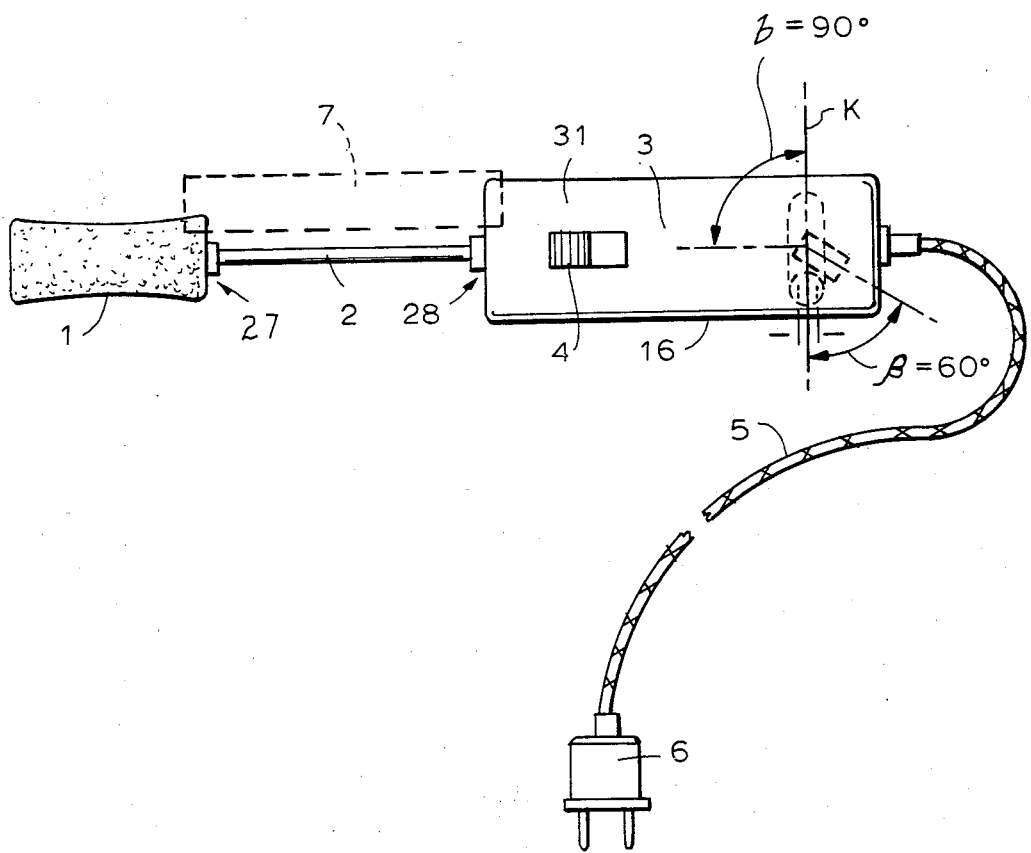
FIG. 1 is a schematic side view of the electric toothbrush according to the invention.

Referring now to the drawings, and first to FIG. 1, it is seen that an electric toothbrush according to the invention includes a rotary elongated brush body 1, a housing 3, which serves as a handle for a user, and an intermediate element 2 which is coupled to a coupling 28 immediately connected to an outlet shaft of an electromotor positioned in the housing 3.

The electromotor is known in the art and for the sake of simplicity is not shown herein.

Reference numeral 7 denotes a protecting cover for protecting a user's cheek from contacting rotating elements of the toothbrush. It is, of course understood that protecting cover 7 can be extended to enclose the whole brush body 1. Reference character 5 shows a cable which terminates with a plug 6. A gravity-induced movement-responsive switch 11 is accomodated within the housing 3. The electric toothbrush of the invention is further provided with a hand operated reversing switch 4 located on the outer surface of the housing 3 of the handle.

The switching path of the gravity-responsive switch 11 is straight-lined as seen from FIG. 1. This switching path of this switch forms with a central axis of elongation of housing 3 an angle $\beta$ which may be between 60° and 90°.

If the switching path of the switch 11 is curved as will be explained in detail below the chord of this path is inclined to the axis of elongation at angle $\beta$.

Figure 2:
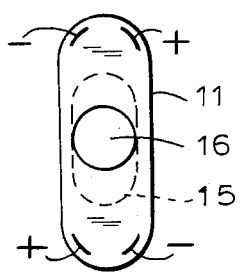
FIG. 2 is an enlarged schematic view of a gravity-induced movement-responsive switch shown in FIG. 1.

With reference to FIG. 2 which schematically illustrates an embodiment of the gravity-responsive switch 11 it can be seen that this switch includes a ball 16 located in the housing of the switch. Ball 16 can be made out of copper, silver, mercury or any other suitable material. The principle of the gravity-responsive switch is that ball 16 falls down under its weight. The inner surface of the housing of switch 11 is provided with contacts marked as "+" and "−" to indicate the electric circuit. When the toothbrush hahdle manipulated by a user is inclined upwardly or downwardly towards the end of the brush 1 the ball 16 falls on the respective one of the lower contacts "+" or "−" so that the electric circuit is closed and the electromotor which drives the rotary brush 1 will be reversed to the right-directed running position, or, respectively left-directed running position. It is understood that if housing 3 is turned, for example about 180°, ball 16 will fall on the oppositely positioned, e.g. upper contacts in the housing of switch 11, and the rotation of the electromotor will be again reversed.

Hand-operated switch 4 serves for switching the electromotor on and off. Such switching, however, may be attained by an additional switch. The primary function of switch 4 in this invention is to switch the toothbrush to a position for cleaning the teeth of an upper jaw or lower jaw. For this purpose a tumbler can be used, which is switched over by a user to its lower position to indicate the toothbrush position for cleaning the lower-jaw teeth or to its upper position to indicate the toothbrush for cleaning the upper-jaw teeth. If the position of the electric toothbrush is not changed by the above switching the direction of rotation of the toothbrush is automatically switched by switch 11.

Further modifications of hand-operated switch designated at 4 in FIG. 1 are illustrated in FIGS. 7 and 8. The switch shown in FIG. 7 includes an actuating pin 23 movably positioned in a tubular rod 22. If spring-loaded (the spring is not shown herein) pin 23 is pressed by a user this leads to actuating of the electric circuit respectively connected to the pin 22 so that the electromotor rotates the right hand direction; the tubular rod 22 maybe additionally pressed by a user to reverse the direction of rotation of the electromotor's shaft and thus toothbrush 1.

The switch shown in FIG. 8 is also hand-operated and is adapted to reverse the direction of running of the electromotor in the fashion similar to that of FIG. 7. The switch includes two keys 25 and 26 with rounded or angular surfaces which are guided in a guide 24 mounted to the housing 3 in any suitable manner. Both keys or pins 25 and 26 are spring-loaded (the springs are not shown herein). The upper surface of pin 25 is concavely curved and can correspond to the running of the electromotor in one direction, for example to the left, whereas the upper surface of pin 26 is convexly curved and may correspond to the running of the electromotor in the opposite direction e.g. to the right. Pins 25 and 26 are selectively pressed by a user to operate the hand-operated switch designated at 4 in FIG. 1. Of course, the indicia other than "to the right" and "to the left" may be provided on the upper or outer surfaces of pins 25 and 26.

Referring back to FIG. 1, it will be seen that coupling of the brush 1 with the electromotor housing 3 via the intermediate element 2 enables one to easily replace the brush 1 on the handle if desired. For this purpose brush 1 with the intermediate element 2 is merely pulled out from the housing or handle 3. For the sake of convenience the replaceable brush and intermediate element may be painted the same color so that the handle or drive unit 3 can be used for the whole family whereas each individual brush with the intermediate element of a certain color may be used by an individual member of the family.

Figure 1A:
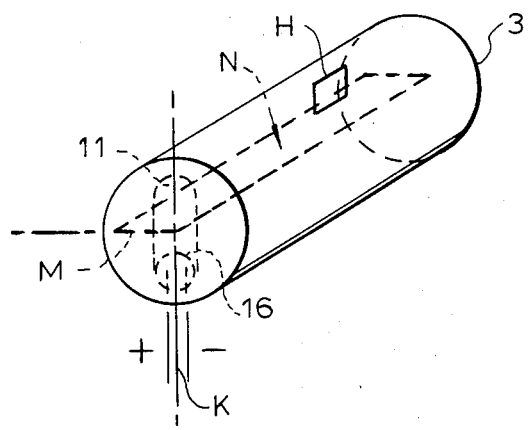
FIG. 1A is a schematic perspective view of the housing of the toothbrush of FIG. 1, with two switches schematically shown.

As seen in FIG. 1A contacts marked as "+" and "−" project into the housing of switch 11 so that ball 16, preferably mercury ball, takes a position against the contacts as shown in the drawing.

Protecting cover 7 can serve as a guide plate for the intermediate element 2.

A falling element 15 shown by dotted lines in FIG. 2 is rounded at its ends. The housing of the switch 11 is so formed that either ball 16 or element 15 which may be provided in place of ball 16 can freely move in the housing of the switch; respective contacts "+" and "−" are provided in the housing of switch 11 illustrated in the toothbrush assembly in FIGS. 1 and 1a; these contacts or contact surfaces may be formed as contact shells with isolated wires.

Figure 3:
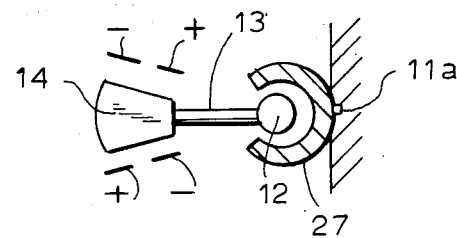
FIG. 3 is a schematic view of the gravity-induced movement-responsive switch of another embodiment of the invention.

The gravity-induced movement switch shown in FIG. 3 includes a shell or bearing 27 with which a ball-like element 12 cooperates upon different positions of its connecting rod 13. Connecting rod 13 carries a contact element 14. Bearing 27 is open in the direction of the connecting rod 13. In the illustrated position contact element 14 will fall downward so as to contact the lower contacts and to thus close the circuit of the electromotor and cause, for example a left-directed running. When the device is turned 180° contact element 14 will take an opposite contact position so as to cause the right-directed running of the electromotor. Shell or bearing 27 is mounted on a wall 11a of the housing of the switch 11.

Figure 4:
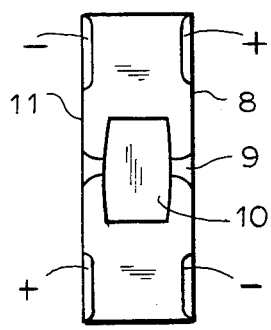
FIG. 4 illustrates still another modification of the switch.

In the embodiment of FIG. 4, a gravity-responsive switch 11 includes a contact element 10 adapted to move in a guide 9 on the housing of switch 11. The contact surfaces marked "+" and "−" are in this embodiment shown as contact blades or springs.

Figure 5:
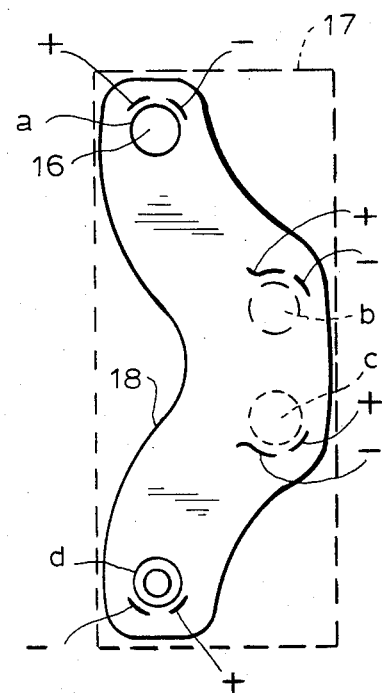
FIG. 5 is a schematic view of yet another embodiment of the switch.

FIG. 5 shows a further embodiment of the gravity-responsive switch, which can be incorporated in the brush body 1 (FIG. 1). This switch is adapted to switch the electromotor to a number of different velocities. The switch includes an isolated housing 17 in which a guide 18 of a predetermined shape for guiding ball 16 is located. In the position "c" of the ball 16 a number of revolutions of the electromotor is for. example, reduced to about 50%. Both lower positions ('c'/"d") corespond to the right-directed running whereas positions indicated as "a"/"b" correspond to the left-directed running when the switch is turned over 180°.

If, for example, the switch is so tilted by a user that ball 16 falls from the position "a" to the position "c" the number of revolutions of the electromotor is reduced to about half. During further tilting of the device, the switch ball 16 falls from the position "c" to the position "d". In further rotation of the device the switch ball 16 moves accordingly in the opposite direction. Guide 18 is isolated and so formed that ball 16 is always guided in a proper position.

Figure 6:
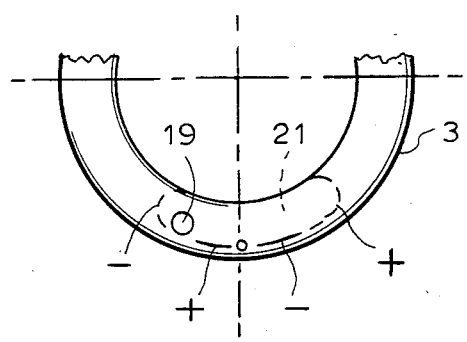
FIG. 6 is a schematic view of a further embodiment of the switch.

The switch shown in FIG. 6 is incorporated in the housing 3 of the electromotor. Guide 21 for guiding a ball 19 may be cast integral with housing 3. Respective contact surfaces are denoted "+" and "−". Ball 19 upon tilting of the device to a certain position contacts a respective one of the contacts "+" and "−" 11 on the surface of guide 21 and closes the electric circuit so as to cause the rotation of the electromotor shaft and the brush in either of two opposite directions. This gravity-induced movement responsive switch has an advantage that housing 3 must be tilted only at a minimal angle, for example 5° to 15° in order to change the direction of rotation of the electromotor. It should be noted that any conventional gravity-induced movement responsive switch may be mounted in the toothbrush handle in the above-described fashion.

The switching path forms with an axis of elongation of housing 3 an angle between 60° and 90°.

A conventional inertia responsive switch may be employed in the electric toothbrush of the invention, which operates upon rotation of the contact element as has been described above.

A liquid-operated switch may be used instead of the above mentioned gravity-responsive or inertia-responsive switches.

An inclined surface 31 formed on the outer wall of housing 3 as shown in FIG. 1 extends in the direction of the intermediate element 2. Hand-operated switch 4 is arranged on that inclined surface 31 to enable a user to easily detect that the lower position of the switch 4 corresponds to the rotation of the motor shaft to the left and thus to the position for cleaning a row of teeth and that the upper position of switch 4 corresponds to the rotation of the motor shaft to the right and thus to the position for cleaning an upper row of teeth.

As clearly seen from the above description the reversing of rotation of the electromotor for cleaning either the upper jaw teeth or the lower jaw teeth is attained by manually operated switch 4. If one needs to switch the position of the toothbrush from the upper row teeth to the lower row teeth and maintain the toothbrush in the same position (without tilting and rotating), the direction of rotation of the electromotor is then reversed simultaneously.

The changing of the direction of rotation of the electromotor can be also attained by operating the gravity-induced movement-responsive switch by changing the position of the whole deivce, for example by rotating it over 180°.

FIG. 9 illustrates the structure of the intermediate element 2a which is formed as a tubular member provided at two ends thereof with couplings 27 and 28 which mesh with respective axles 29 and 30 each formed with a spur-gearing to provide a force-locking connection between the electromotor shaft and brush 1.

It will be understood that each of the elements described above, or two or more together, may also find a useful application in other types of electric toothbrushes differing from the types described above.

While the invention has been illustrated and described as embodied in an electric toothbrush, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a motor driven electric toothbrush comprising an elongated housing serving as a grip and accomodating an electric motor having a drive shaft; a rotary brush connected to an end of said drive shaft; at least one gravity-induced movement-responsive first switch positioned in said housing and having a switching path formed between two end points serving as contacts of said first switch, and a second switch, each switch being formed for switching a direction of rotation of said brush, the improvement comprising said second switch being a manually actuated hand switch having an actuating element, said housing having a side wall, said second switch being positioned on said side wall, said switching path being curved, a plane in which said end points of said switching path is located forming with an axis of elongation of said housing an angle between 60° and 90°, said housing including a guide forming said switching path, and a contact element movable in said guide and adapted to contact a respective one of said contacts depending on the position of said housing, said guide being formed so that said housing may be turned at an angle between 5° to 15° to change the direction of rotation of said brush.

2. The toothbrush as defined in claim 1, wherein said contact element is a ball.

3. The toothbrush as defined in claim 1, wherein said two end points serving as contacts of said first switch are provided on said guide.

* * * * *